United States Patent [19]

Heath et al.

[11] 4,005,026
[45] Jan. 25, 1977

[54] DETERGENT COMPOSITIONS CONTAINING NOVEL CRYSTALLINE FORMS OF OPTICAL BRIGHTENERS

[75] Inventors: James C. Heath, Norwood; Raymond E. Werner, Blue Ash, both of Ohio; John W. Delaney, Fort Mitchell, Ky.; Nathan N. Crounse, Cincinnati, Ohio

[73] Assignee: Sterling Drug Inc., New York, N.Y.

[22] Filed: Sept. 5, 1975

[21] Appl. No.: 610,629

Related U.S. Application Data

[63] Continuation-in-part of Ser. No. 834,560, June 18, 1969, Pat. No. 3,951,960, which is a continuation-in-part of Ser. No. 526,351, Feb. 10, 1966, abandoned, which is a continuation-in-part of Ser. No. 283,558, May 27, 1963, abandoned, which is a continuation-in-part of Ser. No. 177,743, March 6, 1962, abandoned.

[52] U.S. Cl. ................................ 252/89 B; 252/94; 252/98; 252/99; 252/543; 260/240 B
[51] Int. Cl.² ...................... C11D 3/28; C11D 7/32; C11D 7/34
[58] Field of Search ................ 252/543, 94, 89, 98, 252/99; 260/240 B

[56] References Cited

FOREIGN PATENTS OR APPLICATIONS

| 1,100,583 | 3/1961 | Germany | 260/240 A |
|---|---|---|---|
| 2,061,863 | 6/1972 | Germany | 252/94 |
| 1,337,583 | 11/1971 | United Kingdom | 252/543 |
| 1,286,073 | 8/1972 | United Kingdom | 252/543 |
| 1,210,952 | 2/1968 | United Kingdom | 252/543 |

*Primary Examiner*—Mayer Weinblatt
*Assistant Examiner*—Edith R. Buffalow
*Attorney, Agent, or Firm*—Lynn T. Fletcher; B. Woodrow Wyatt

[57] ABSTRACT

Novel crystalline needle forms of the fluorescent compounds disodium 4,4'-bis(4-anilino-6-morpholino-s-triazin-2-ylamino)-2,2'-stilbenedisulfonate and disodium 4,4'-bis(4,6-dianilino-s-triazin-2-ylamino)-2,2'-stilbenedisulfonate, useful as optical brightening agents, particularly when incorporated into detergent compositions. The novel crystalline forms are prepared by heating the compound in an aqueous alkaline medium containing excess amine reactant.

3 Claims, No Drawings

DETERGENT COMPOSITIONS CONTAINING NOVEL CRYSTALLINE FORMS OF OPTICAL BRIGHTENERS

This application is a continuation-in-part of our prior copending application Ser. No. 834,560 now U.S. Pat. No. 3,951,960, filed June 18, 1969, which in turn is a continuation-in-part of our now-abandoned application Ser. No. 283,558, filed May 27, 1963 and of our now abandoned application Ser. No. 526,351, filed Feb. 10, 1966, which latter application was a continuation-in-part of our now abandoned application Ser. No. 177,743, filed Mar. 6, 1962.

BACKGROUND OF THE INVENTION a. Field of the Invention

This invention relates to salts of the fluorescent compounds 4,4'-bis(4-anilino-6-morpholino-s-triazin-2-ylamino)-2,2'-stilbenedisulfonic acid and 4,4'-bis(4,6-dianilino-s-triazin-2-ylamino)-2,2'-stilbenedisulfonic acid novel crystalline forms having improved properties as optical bleaching agents, to new articles of manufacture containing said salts in the novel forms, to detergent compositions containing said salts in the novel forms, and to the preparation of same.

b. Description of the Prior Art

Disodium 4,4'-bis(4-anilino-6-morpholino-s-triazin-2-ylamino)-2,2'-stilbenedisulfonate (Formula I)

brightening agent have been described in the prior art, for example, in Japanese Pat. No. 3988/51, issued July 24, 1951, and in German Auslegeschrift 1,100,583, issued Mar. 2, 1961. The prior art teaches that these compounds are ordinarily prepared in the following manner. One molecular proportion of disodium 4,4'-diaminostilbene-2,2'-disulfonate is condensed with two molecular proportions of cyanuric chloride at low temperature (0–5° C); then, in the case of the compound of Formula I, one molecular proportion of the resulting disodium 4,4'-bis(4,6-dichloro-s-triazin-2-ylamino)-2,2'-stilbenedisulfonate is aminated with two molecular proportions of aniline or morpholine at approximately 50° C; and one molecular proportion of the resulting product, that is, disodium, 4,4'-bis(4-chloro-6-anilino-s-triazin-2-ylamino)-2,2'-stilbenedisulfonate or disodium 4,4'-bis(4-chloro-6-morpholino-s-triazin-2-ylamino)-2,2'-stilbenedisulfonate is aminated at 95°–100° C with two molecular proportions of either morpholine or aniline, respectively, to produce disodium 4,4'-bis(4-anilino-6-morpholino-s-triazin-2-ylamino)-2,2'-stilbenedisulfonate. In the case of the compound of Formula II, the intermediate disodium 4,4'-bis(4,6-dichloro-s-triazin-2-ylamino)-2,2'-disulfonate is interacted with aniline at a somewhat higher temperature (usually in the range 30°–100° C) to replace the four chloro substituents with four anilino groups. In each of these steps, sufficient alkali is added to the reaction mixture to keep it substantially neutral during the reaction.

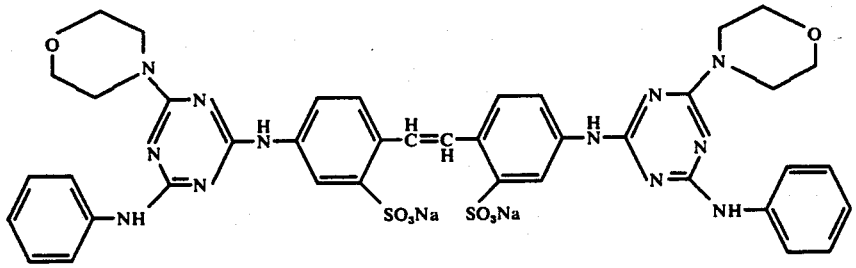

Formula I and disodium 4,4'-bis(4,6-dianilino-s-triazin-2-ylamino)-2,2'-stilbenedisulfonate (Formula II)

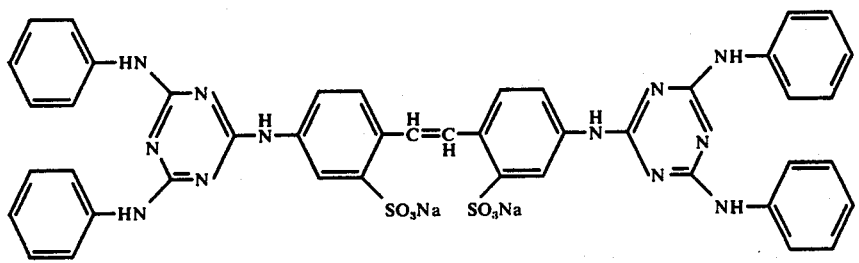

Formula II are known compounds which have valuable properties as fluorescent optical bleaching agents in detergent compositions for the laundering of textile goods. The dianilino-, dimorpholino-substituted compound of Formula I, its preparation and utility as an optical bleach have been described, for example, in U.S. Pat. No. 2,612,501, patented Sept. 30, 1952. Similarly, the tetra-anilino-substituted compound of Formula II, its preparation and utility as an optical whitening and As produced by this known method of manufacture, the disodium 4,4'-bis(4-anilino-6-morpholino-s-triazin-2-ylamino)-2,2'-stilbenedisulfonate is a pale yellow amorphous (non-crystalline) solid. This amorphous product has the drawback of being light-sensitive, changing from yellow to green to brown during relatively short exposures to light, for instance, one to two hours. The light sensitivity is objectionable, especially when the product is to be incorporated into white detergents. As produced by the known method of manufacture, disodium 4,4'-bis(4,6-dianilino-s-triazin-2-ylamino)-2,2'-stilbenedisulfonate is a yellow solid which is usually marketed and used in the light-sensitive amorphous form in which it is initially obtained by the above method or, in some instances, the amorphous form has been converted into a yellow crystalline form consisting predominantly of a plate-like crystalline form. Furthermore, German Auslegeschrift 1,100,583 discloses a method for producing the compound in the form of a mixture of plates and crystalline rods or needles which is yellow and undesirable for the manufacture of detergent compositions. When any of these forms of the product is incorporated into detergent compositions, it has the drawback of poor resistance to chemical attack by the hypochlorite bleach commonly added during laundering, so that a substantial proportion of the whitening and brightening effect is destroyed. Moreover, in many instances, it has been found that they impart an undesirable yellow cast to white solid detergent compositions.

SUMMARY OF THE INVENTION

In one of its composition aspects, this invention resides in a compound selected from the group consisting of di-sodium 4,4'-bis(4-anilino-6-morpholino-s-triazin-2-ylamino)-2,2'-stilbenedisulfonate in the form of cyrstalline needles and disodium 4,4'-bis(4,6-dianilino-s-triazin-2-ylamino)-2,2'-stilbenedisulfonate in improved crystalline needle forms characterized by their X-ray diffraction data and indices of refraction. In another of its composition aspects, the invention resides in a soap or detergent composition having incorporated therein an effective brightening amount of a compound selected from the group consisting of disodium 4,4'-bis(4-anilino-6-morpholino-s-triazin-2-ylamino)-2,2'-stilbenedisulfonate and disodium 4,4'-bis(4,6-dianilino-s-triazin-2-ylamino)-2,2'-stilbenedisulfonate in the form of said novel crystalline needles. In one of its process aspects, this invention resides in the method which comprises heating, at a temperature in the approximate range 90°–200° C, amorphous disodium 4,4'-bis-4-anilino-6-morpholino-s-triazin-2-ylamino)-2,2'-stilbenedisulfonate with one-half to five molecular proportions of aniline or morpholine in an aqueous medium having an initial pH in the range of 8 to 12 until approximately 80 to 100 percent of the disodium 4,4'-bis(4-anilino-6-morpholino-s-triazin-2-ylamino)-2,2'-stilbenedisulfonate is in the form of crystalline needles. In another of its process aspects, the invention resides in the method which comprises heating, at a temperature in the approximate range 90°–200° C, an amorphous or plate form of disodium 4,4'-bis(4,6-dianilino-s-triazin-2-ylamino)-2,2'-stilbenedisulfonate with from one to five molecular proportions of aniline in an aqueous medium having an initial pH in the approximate range 8 to 12 until approximately 80 to 100 percent of the disodium 4,4'-bis(4,6-dianilino-s-triazin-2-ylamino)-2,2'-stilbenedisulfonate is in the form of birefringent crystalline rods.

DETAILED DESCRIPTION INCLUSIVE OF THE PREFERRED EMBODIMENTS

It is a particular object of the instant invention to increase the effectiveness and value of disodium 4,4'-bis(4-anilino-6-morpholino-s-triazin-2-ylamino)-2,2'-stilbenedisulfonate and disodium 4,4'-bis(4,6-dianilino-s-triazin-2-ylamino)-2,2'-stilbenedisulfonate as whitening and brightening agents, by providing the said compounds in a novel and improved crystalline form in which the drawbacks pointed out above are minimized.

In accordance with the instant invention, we produce disodium 4,4'-bis(4-anilino-6-morpholino-s-triazin-2-ylamino)-2,2'-stilbenedisulfonate and disodium 4,4'-bis(4,6-dianilino-s-triazin-2-ylamino)-2,2'-stilbenedisulfonate either largely or wholly, as desired, in the form of white to light cream colored needle-shaped crystals which can be readily distinguished qualitatively from the old amorphous form either by simple visual examination under a microscope or by determination of the characteristic X-ray diffraction powder pattern. The art of crystallography generally refers to crystals in this novel form either as needles or rods, and the two terms, being equivalent, are used interchangeably. The novel crystalline rod or needle form of disodium 4,4'-bis(4-anilino-6-morpholino-s-triazin-2-ylamino)-2,2'-stilbenedisulfonate shows excellent light stability, its color being virtually unaffected by the same exposures to ultraviolet light which produces an easily discernible discoloration of the amorphous forms.

When viewed with a polarizing microscope equipped with crossed Nicol prisms, the amorphous forms of disodium 4,4'-bis(4-anilino-6-morpholino-s-triazin-2-ylamino)-2,2'-stilbenedisulfonate appear as agglomerates of powder which transmit no light. X-ray diffraction pictures, obtained by the powder method using nickel filtered copper $K_\alpha$ radiation, show for the amorphous forms of the compound only a diffuse grey pattern, as is characteristic of associated molecules lacking an ordered state, whereas the new crystalline needle form shows characteristic diffraction patterns.

Like the amorphous forms, the crystalline needle forms of disodium 4,4'-bis(4-anilino-6-morpholino-s-triazin-2-ylamino)-2,2'-stilbenedisulfonate and disodium 4,4'-bis-(4,6-dianilino-s-triazin-2-ylamino)-2,2'-stilbenedisulfonate do not melt when heated at high tempertures, for example, up to 300° C.

DISODIUM 4,4'-BIS(4-ANILINO-6-MORPHOLINO-S-TRIAZIN-2-YLAMINO)-2,2'-STILBENEDISULFONATE

The solutions of the needle form and the amorphous form of disodium 4,4'-bis(4-anilino-6-morpholino-s-triazin-2-ylamino)-2,2'-stilbenedisulfonate are not distinguishable from each other on the basis of ultraviolet absorption curves. When the solids are viewed under ultraviolet light, the amorphous form as commercially produced has a dull greenish-yellow color, and the needle form has a bluish-white color.

The needle form of the compound, however, shows a characteristic diffraction pattern with the following interplanar spacings, obtained by the powder method using nickel-filtered copper $K_\alpha$ radiation:

| INTERPLANAR SPACINGS, A. |
|---|
| 26.75 |
| 10.04 |
| 9.20 |
| 8.42 |
| 6.02 |
| 5.34 |
| 5.18 |
| 4.79 |
| 4.35 |
| 4.29 |

In accordance with our invention, the production of disodium 4,4'-bis(4-anilino-6-morpholino-s-triazin-2-ylamino)-2,2'-stilbenedisulfonate in the form of crystalline needles can be accomplished by employing as the starting material the conventional amorphous form which is the product obtained by using the known procedure, as outline above, for replacing by amination the four chloro substituents in disodium 4,4'-bis(4,6-dichloro-s-triazin-2-ylamino)-2,2'-stilbenedisulfonate with two anilino and two morpholino substituents. Advantageously, the starting amorphous disodium 4,4'-bis(4-anilino-6-morpholino-s-triazin-2-ylamino)-2,2'-stilbenedisulfonate is used directly in the form of the water-wet pulp produced by the amination reactions. Our new method comprises heating, at a temperature in the approximate range 90°–200° C, amorphous disodium 4,4'-bis(4-anilino-6-morpholino-s-triazin-2-ylamino)-2,2'-stilbenedisulfonate with approximately one-half to five molecular proportions of an amine of the group consisting of aniline and morpholine in an aqueous medium having an initial pH in the approximate range 8 to 12 until all or a substantial proportion (for instance, 80 percent or more) of the disodium 4,4'-(4-anilino-6-morpholino-s-triazin-2-ylamino)-2,2'-stilbenedisulfonate is in the form of crystalline needles. This heating can be carried out under atmospheric pressure at a temperature in the range from approximately 90° C to reflux temperature (about 100° C), or in an autoclave at a temperature up to approximately 200° C. Substantially complete conversion to the crystalline needle form is usually effected within 3 to 4 hours at most, and under optimum conditions is effected within twenty minutes or less. The product is readily recovered from the aqueous suspending medium for instance, by filtration.

When atmospheric pressure is employed in our method, we prefer to mix approximately two and one-half to five (advantageously, about three to four) moles of aniline or morpholine (or, if desired, mixture thereof) with each mole of amorphous disodium 4,4'-bis(4-anilino-6-morpholino-s-triazin-2-ylamino)-2,2'-stilbenedisulfonate, the latter as a 5 to 20 percent (advantageously, about 10 percent) slurry in water, adjust the pH of the aqueous medium to approximately 8.5–9.5 with sodium hydroxide or a suitable basic sodium salt as an equivalent thereof, and then heat the resulting mixture at reflux temperature until substantially all of the disodium 4,4'-bis(4-anilino-6-morpholino-s-triazin-2-ylamino)-2,2'-stilbenedisulfonate is in crystalline needle form.

When an autoclave is employed in our new method, we prefer to mix approximately one-half to three (advantageously, about one) moles of aniline or morpholine (if desired, mixtures of the two) with each mole of amorphous disodium 4,4'-bis(4-anilino-6-morpholino-s-triazin-2-ylamino)-2,2'-stilbenedisulfonate, the latter as a 5 to 20 percent (advantageously, about 10 percent) slurry in water, adjust the pH of the aqueous medium to approximately 10.0–10.5 with sodium hydroxide or a suitable basic sodium salt as an equivalent thereof, and then heat the resulting mixture at 125°–175° C until substantially all of the disodium 4,4'-bis(4-anilino-6-morpholino-s-triazin-2-ylamino)-2,2'-stilbenedisulfonate is in crystalline needle form.

We have found that the presence of inorganic salts such as sodium chloride in unpurified amorphous starting material slows down the conversion to the crystalline needle form somewhat, and under such circumstances, a heating period of about four hours may be required even when the conversion conditions are otherwise optimum. Despite this lengthening of the heating period, which can be readily obviated by use of conventional purification procedures, it is usually more economical in commercial production to use a slightly impure starting material (that is, wherein the percentage of inorganic salts is no more than about 10 percent) as such rather than incur the losses attendant to purification procedures.

In addition to having excellent light-stability, the novel crystalline needle form of disodium 4,4'-bis(4-anilino-6-morpholino-s-triazin-2-ylamino)-2,2'-stilbenedisulfonate afforded by our invention also has improved optical bleaching properties, as compared with the corresponding known amorphous form, when used in detergent compositions to launder cotton fabrics in the presence of hypochlorite bleach. Thus, for example, under these conditions, we found that when the novel needle form of disodium 4,4'-bis(4-anilino-6-morpholino-s-triazin-2-ylamino)-2,2'-stilbenedisulfonate was used the loss of whitening effect due to action of sodium hypochlorite bleach was only about 80 percent as great as the loss incurred when the amorphous form of disodium 4,4'-bis(4-anilino-6-morpholino-s-triazin-2-ylamino)-2,2'-stilbenedisulfonate was used.

DISODIUM 4,4'-BIS(4,6-DIANILINO-S-TRIAZIN-2-YLAMINO)-2,2'-STILBENEDISULFONATE

In accordance with the novel methods of the instant invention hereinafter described, we produce disodium 4,4'-bis(4,6-dianilino-s-triazin-2-ylamino)-2,2'-stilbenedisulfonate either largely or wholly, as desired, in the form of novel rod-shaped crystals. At least two distinct rod-like crystalline forms (A and B) are produced according to the processes described herein. The crystalline rod form produced in preponderant quantities is determined by the particular choice of reaction conditions employed within the range of conditions described herein.

The novel crystals are small, white, birefringent rods in which the lowest index of refraction is parallel to the long axis of the rod. In rod form A, this index has a value between 1.53 and 1.54; in the rod form B, the corresponding index has a value between 1.88 and 1.94. The value for the other index (or indices) in each of the rod forms is greater than 1.70. Since only parallel extinction can be noted in the rod forms they belong to either the tetragonal or the orthorhombic system.

We have found that crystalline rod form A tends to crystallize in two modifications: one contains up to about six percent water which appears to be in the crystalline lattice, and the other is substantially anhydrous (containing approximately 0.8 percent water). The indices of refraction of the two modifications are the same, thus offering a means of identification of the crystals as rod form A. However, the X-ray diffraction patterns of the two modifications of rod form A show distinct differences in the crystalline structure, as set forth more fully below. No other differences in the physical properties of the two modifications have been observed.

The novel crystalline rod forms of disodium 4,4'-bis(4,6-dianilino-s-triazin-2-ylamino)-2,2'-stilbenedisulfonate provided by this invention can be readily distinguished qualitatively from the old crystalline plate form or amorphous form either by simple visual examination under a microscope or by determination of the characteristic X-ray diffraction powder patterns.

The crystalline plate form of disodium 4,4'-bis(4,6-dianilino-s-triazin-2-ylamino)-2,2'-stilbenedisulfonate appears as elongated, roughly rectangular plates. These crystals have a strong propensity for formation of overgrowths or possibly twinned crystals together with lack of visible details of other than the two primary faces, so that a study of the crystal geometry is made difficult.

A quantitative differentiation between the new rod forms and the previously known plate form can be made by comparison of interplanar spacings as shown by the X-ray diffraction data, set forth below, obtained in each instance by the powder method using nickel filtered copper $K_\alpha$ radiation. Moreover, the rod forms are differentiated from one another by their individual characteristic X-ray diffraction patterns. Rod form A containing water and the substantially anhydrous rod form A have individual X-ray diffraction patterns as shown. Rod form B is characterized by five prominent lines in the diffraction pattern as shown.

| INTERPLANAR SPACINGS, A. | | | |
|---|---|---|---|
| Rod Form A (Hydrated form) | Rod Form A (Anhydrous form) | Rod Form B | Plate Form |
| 6.23 | 17.6 | 13.2 | 6.72 |
| 5.90 | 16.6 | 5.78 | 6.30 |
| 5.70 | 13.6 | 4.96 | 5.99 |
| 5.59 | 9.50 | 4.52 | 5.57 |
| 5.51 | 6.80 | 3.88 | 5.32 |
| 5.34 | 5.53 | | 5.00 |
| 4.90 | 5.33 | | 4.76 |
| 4.85 | 3.96 | | 4.52 |
| 4.60 | | | 4.08 |
| 3.98 | | | 3.88 |
| 3.82 | | | 3.72 |
| 3.64 | | | 3.67 |
| 3.44 | | | 3.61 |
| 3.28 | | | 3.48 |
| 3.22 | | | 3.39 |
| | | | 3.26 |
| | | | 3.18 |
| | | | 3.04 |

The amorphous (non-crystalline) form of disodium 4,4'-bis(4,6-dianilino-s-triazin-2-ylamino)-2,2'-stilbendisulfonate is readily distinguished from the crystalline plate and rod forms by viewing them with a polarizing microscope equipped with crossed Nicol prisms. When so viewed, the amorphous form appears as agglomerates of powder which transmit no light. An X-ray diffraction picture of the amorphous form shows only a diffuse grey pattern, as is characteristic of associated molecules lacking an ordered state.

The solutions of the rod, plate, and amorphous forms are not distinguishable from each other on the basis of ultraviolet absorption curves. When the solids are viewed under ultraviolet light, the amorphous and the plate forms have a pale blue color, the latter being of greater intensity of brightness, and the rod forms each have a violet color with low intensity of brightness.

As stated above, German Auslegeschrift 1,100,583 discloses a process of preparing disodium 4,4'-bis(4,6-dianilino-s-triazin-2-ylamino)-2,2'-stilbenedisulfonate and the product so prepared is characterized as a mixture of plates and rods having inferior properties. Furthermore, the X-ray diffraction pattern of the product produced in accordance with the German Auslegeschrift procedure is entirely different from the X-ray diffraction patterns of our improved forms. Following are the interplanar spacings of the product prepared in accordance with the German Auslegeschrift procedure:

| INTERPLANAR SPACINGS, A. |
|---|
| 26.36 |
| 17.31 |
| 13.38 |
| 6.75 |
| 5.30 |

In accordance with our invention, the production of disodium 4,4'-bis(4,6-dianilino-s-triazin-2-ylamino)-2,2'-stilbenedisulfonate in either of the crystalline rod forms can be accomplished by employing as the starting material the conventional amorphous form which is the product obtained by using any of the published procedures for carrying out the interaction of disodium 4,4'-bis(4,6-dichloro-s-triazin-2-ylamino)-2,2'-stilbenedisulfonate with aniline; or alternatively, we can use the crystalline plate form, which we have found can be produced by slurrying the amorphous form in a mixture of water and acetone, refluxing the slurry for an hour or so, making the mixture barely alkaline to phenolphthalein by adding 50 percent aqueous sodium hydroxide solution, refluxing the mixture for another hour or so, and then filtering the mixture to recover the crystalline plate form. Our new method of preparing the novel rod forms comprises heating, at a temperature in the approximate range 90°–200° C, the amorphous form or the crystalline plate form of disodium 4,4'-bis(4,6-dianilino-s-triazin-2-ylamino)-2,2'-stilbenedisulfonate, or a mixture of the amorphous and crystalline plate form, with approximately one to five molecular proportions of aniline in an aqueous medium having an initial pH in the approximate range 8 to 12 until all or a substantial proportion (for instance 80 percent or more) of the disodium 4,4'-bis(4,6-dianilino-s-triazin-2-ylamino-2,2'-stilbenedisulfonate is in the form of crystalline rods. Substantially complete conversion to crystalline rod form is usually effected within three to four hours at most, and under optimum conditions is effected within twenty minutes or less. The product is readily recovered from the aqueous suspending medium, for instance by filtration. This heating can be carried out under atmospheric pressure at a temperature in the range from approximately 90° C to reflux temperature (about 100° C), or in an autoclave at a temperature up to approximately 200° C.

When atmospheric pressure is employed in our method, we prefer to mix approximately two and one-half to five (advantageously, about three to four) moles of aniline with each mole of amorphous or crystalline plate form of disodium 4,4'-bis(4,6-dianilino-s-triazin-2-ylamino)-2,2'-stilbenedisulfonate, the latter as a 5 to 20 percent (advantageously, about 10 percent) slurry in water, adjust the pH of the aqueous medium to approximately 8.5–9.5, with sodium hydroxide or a suitable basic sodium salt as an equivalent thereof, and then heat the resulting mixture at reflux temperature until substantially all of the disodium 4,4'-bis(4,6-dianilino-s-triazin-2-ylamino)-2,2'-stilbenedisulfonate is in crystalline rod form. The crystalline form produced in this way is rod form A.

When an autoclave is employed in our new method, we prefer to mix approximately one to three (advantageously, about two) moles of aniline with each mole of amorphous or crystalline plate form of disodium 4,4'-bis(4,6-dianilino-s-triazin-2-ylamino)-2,2'-stilbenedisulfonate, the latter as a 5 to 20 percent (advantageously, about 10 percent) slurry in water, adjust the pH of the aqueous medium to approximately 10.0–10.5 with sodium hydroxide or a suitable basic sodium salt as an equivalent thereof, and then heat the resulting mixture at 135°–175° C until substantially all of the disodium 4,4'-bis(4,6-dianilino-s-triazin-2-ylamino)-2,2'-stilbenedisulfonate is in crystalline rod form. The crystalline form produced in this manner is rod form B described above.

The relative proportions of rod form A and rod form B produced in the instant process are dependent primarily upon the reaction temperature. Thus, below 135° C, a preponderance of rod form A is generally produced, and above 135° C, a preponderance of rod form B is produced. However, rod form B can be obtained at lower temperatures, for example, about 125° C, by employing a somewhat larger quantity of aniline, for example, from four to five molecular equivalents for each molecular equivalent of brightener.

We have found that the presence of inorganic salts such as sodium chloride in unpurified amorphous or crystalline plate starting material slows down the conversion to crystalline rod form somewhat, and under such circumstances, a heating period of about four hours may be required even when the conversion conditions are otherwise optimum. Despite this lengthening of the heating period, which can be readily obviated by use of conventional purification procedures, it is usually more economical in commercial production to use a slightly impure starting material (that is, wherein the percentage of inorganic salts is no more than about 5 percent) as such rather than incur the losses attendant to purification procedures.

The novel crystalline rod forms of disodium 4,4'-bis(4,6-dianilino-s-triazin-2-ylamino)-2,2'-stilbenedisulfonate afforded by our invention unexpectedly have substantially improved optical bleaching properties, as compared with the corresponding conventional amorphous and crystalline plate forms and the known crystalline plate and rod-form mixture. Thus, when the amorphous, crystalline plate, and crystalline rod forms are incorporated into detergent compositions which are then used in a conventional textile laundering procedure wherein a hypochlorite bleaching agent is used, we have found that our novel crystalline rod forms are much more stable than the old amorphous and crystalline plate forms toward the destructive action of the hypochlorite bleaching agent. This increased stability when the novel crystalline rod forms are used results in a significant increase in the whitening and brightening effect produced on the textiles. Moreover, the novel crystalline rod forms are not only free of any undesirable yellowing effect on white solid detergent compositions when incorporated therein at concentration levels of practical use but, to the contrary, in many instances they have a desirable whitening effect which improves the appearance of such detergent compositions.

Our invention is illustrated by the following examples without, however, being limited thereto.

EXAMPLE 1

A slurry of 9.2 g of yellow amorphous disodium 4,4'-bis(4-anilino-6-morpholino-s-triazin-2-ylamino)-2,2'-stilbenedisulfonate (as an unpurified water-wet pulp obtained by interacting two molecular proportions of morpholine with disodium 4,4'-bis(-dichloro-s-triazin--dichloro-s-triazin-2-ylamino)-2,2'-stilbenedisulfonate and then interacting one molecular proportion of the resultant disodium 4,4'-bis(4-chloro-6-morpholino-s-triazin-2-ylamino)-2,2'-stilbenedisulfonate with two molecular proportions of aniline), 2.3 g of aniline, 90 ml of water, and 5 ml of 1N aqueous sodium hydroxide solution was stirred and heated at reflux temperature (approximately 100° C) for forty-five minutes. The mixture was then filtered while hot (about 90°–95° C) and the solid thus collected was washed with hot (about 80° C) water until the washings were neutral to Brilliant Yellow indicator and colorless. The product was dried at 70° C. There was thus obtained 5.2 g of crystalline white needles of disodium 4,4'-bis(4-anilino-6-morpholino-s-triazin-2-ylamino)-2,2'-stilbenedisulfonate.

EXAMPLE 2

A slurry of 9.2 g of amorphous disodium 4,4'-bis(4-anilino-6-morpholino-s-triazin-2-ylamino)-2,2'-stilbenedisulfonate, 2.2 g of morpholine, 90 ml of water, and 5 ml of 1N aqueous sodium hydroxide solution was stirred and heated at reflux temperature for 45 minutes. The mixture was then filtered while hot and the solid thus collected was washed with hot water until the washings were neutral to Brilliant Yellow indicator and colorless. The product was dried at 70° C. There was thus obtained 4.6 g of cream colored crystalline needles of disodium 4,4'-bis(4-anilino-6-morpholino-s-triazin-2-ylamino)-2,2'-stilbenedisulfonate.

EXAMPLE 3

A slurry of 9.2 g of amorphous disodium 4,4'-bis(4-anilino-6-morpholino-s-triazin-2-ylamino)-2,2'-stilbenedisulfonate, 1.15 g of aniline, 1.1 g of morpholine, 90 ml of water, and 5 ml of 1N aqueous sodium hydroxide solution was stirred and heated at reflux temperature for one and one-quarter hours. The mixture was then filtered while hot and the solid thus collected was washed with hot water until the washings were neutral to Brilliant Yellow indicator and colorless. The product was dried at 70° C. There was thus obtained 5.5 g of cream colored crystalline needles of disodium 4,4'-bis(4-anilino-6-morpholino-s-triazin-2-ylamino)-2,2'-stilbenedisulfonate.

EXAMPLE 4

A slurry of 74 g of amorphous disodium 4,4'-bis(4-anilino-6-morpholino-s-triazin-2-ylamino)-2,2'-stilbenedisulfonate in 600 ml of water was heated to reflux temperature, and sufficient aqueous sodium hydroxide solution was added to make the mixture alkaline to phenolphthalein. There was then added 7.5 g of aniline, and the resulting mixture was heated at 135° C in an autoclave for 2 hours. The reaction mixture was allowed to cool to room temperature and was then filtered. The solid thus collected was washed with a 15 percent aqueous solution of sodium chloride. The product was dried at 70° C. There was thus obtained 70 g of cream to yellow crystalline needles of disodium 4,4'-bis(4-anilino-6-morpholino-s-triazin-2-ylamino)-2,2'-stilbenedisulfonate.

EXAMPLE 5

A mixture of 96 g of amorphous disodium 4,4'-bis(4-anilino-6-morpholino-s-triazin-2-ylamino)-2,2'-stilbenedisulfonate (as as unpurified water-wet pulp obtained by interacting two molecular proportions of morpholine with disodium 4,4'-bis(4,6-dichloro-s-triazin-2-ylamino)-2,2'-stilbenedisulfonate and then interacting one molecular proportion of the resultant disodium 4,4'-bis(4-chloro-6-morpholino-s-triazin-2-ylamino)-2,2'-stilbenedisulfonate with two molecular proportions of aniline), 30 g of aniline, and 1000 ml of water was made alkaline to phenolphthalein by addition of aqueous sodium hydroxide solution, and the mixture was heated at reflux temperature (approximately 100° C) for four hours. The reaction mixture was then filtered while hot and the solid thus collected was washed with 500 ml of hot (85° C) 15 percent aqueous sodium chloride solution. The product was dried at 70° C. There was thus obtained 86.5 g of cream colored crystalline needles of disodium 4,4'-bis(4-anilino-6-morpholino-s-triazin-2-ylamino)-2,2'-stilbenedisulfonate.

EXAMPLE 6

A slurry of 8.5 g of yellow amorphous disodium 4,4'-bis(4,6-dianilino-s-triazin-2-ylamino)-2,2'-stilbenedisulfonate (as an unpurified water-wet pulp obtained by interacting aniline with disodium 4,4'L -bis(4,6-dichloro-s-triazin-2-ylamino)-2,2'-stilbenedisulfonate) in 2.5 g of aniline, 80 ml of water, and 1 ml of 1N aqueous sodium hydroxide solution was heated at reflux temperture (approximately 100° C). During the reflux period, samples were removed periodically from the mixture and examined microscopically. After about one hour of refluxing, rod-shaped crystals were detected in a sample of the mixture. After about three and one-half hours of refluxing virtually all of the solid in the mixture had been converted into rod-shaped crystals and the color of the slurry had changed from light yellow to white. Refluxing of the mixture was continued until the total reflux time was about five and three-quarters hours. The mixture was then filtered while hot (about 90°-95° C) and the white solid thus collected was washed with hot (about 80° C) water until the washings were neutral to Brilliant Yellow indicator and colorless. The product was dried at 70° C. There was thus obtained 8.4 g of white rod-shaped crystals of disodium 4,4'-bis(4,6-dianilino-s-triazin-2-ylamino)-2,2'-stilbenedisulfonate. X-ray diffraction data for this product correspond to the data given above for hydrated rod form A.

EXAMPLE 7

Disodium 4,4'-bis(4,6-dichloro-s-triazin-2-ylamino)-2,2'-stilbenedisulfonate was prepared by interaction of 500 pounds of 4,4'-diamino-2,2'-stilbenedisulfonic acid with a solution of 500 pounds of cyanuric chloride in 2100 pounds of acetone in an aqueous reaction medium at pH 7–8 prepared by mixing 3200 pounds of crushed ice and approximately 2100 pounds of 10 percent aqueous sodium hydroxide solution. The disodium 4,4'-bis(4,6-dichloro-s-triazin-2-ylamino)-2,2'-stilbenedisulfonate thus obtained was mixed with 270 pounds of disodium phosphate and interacted at 15°–50° C with 625 pounds of aniline for thirty minutes and then the pH of the reaction mixture was adjusted to 6.7–6.8 by adding approximately 600 pounds of 10 percent aqueous sodium hydroxide solution during a period of one hour.

The yellow amorphous disodium 4,4'-bis(4,6-dianilino-s-triazin-2-ylamino)-2,2'-stilbenedisulfonate obtained as described above contained approximately 2.6 percent of sodium chloride and 1.3 percent of disodium phosphate. To a 10 percent aqueous slurry of this product remaining after distilling off substantially all of the acetone in a 1800 gallon stainless steel pressure kettle there was added 125 pounds of aniline. The pH of the resulting mixture was adjusted to 10.5 by addition of approximately 200 pounds of 50 percent aqueous sodium hydroxide solution. The mixture was stirred at 85° C for thirty minutes with the kettle open, and then after checking to assure that the pH was still 10.5 the kettle was closed. The mixture was heated at 125° C for four hours and was then cooled to 100° C. The kettle was vented, and the mixture (which had a pH of 10.3) was pumped into a filter press. The crude product was washed in the press with a hot (95°–100°C) solvent prepared by mixing 800 gallons of water, 50 pounds of sodium chloride, and 12 pounds of 50 percent aqueous sodium hydroxide solution. The press-cake obtained in this manner was washed with a cold solution of 100 pounds of sodium chloride in 800 gallons of water and was then dried. There was thus obtained 1250 pounds of disodium 4,4'-bis(4,6-dianilino-s-triazin-2-ylamino)-2,2'-stilbenedisulfonate in the form of white crystalline rods.

By purification of the amorphous disodium 4,4'-bis(4,6-dianilino-s-triazin-2-ylamino)-2,2'-stilbenedisulfonate used as a starting material in the foregoing method, so that the inorganic salts are removed, the heating period in the autoclave can be reduced to about twenty minutes for substantially complete conversion of the amorphous form to the crystalline rod form. X-ray diffraction data for this product correspond to the data given above for the substantially anhydrous rod form A.

EXAMPLE 8

A slurry of approximately 60 g of yellow amorphous disodium 4,4'-bis(4,6-dianilino-s-triazin-2-ylamino)-2,2'-stilbenedisulfonate (as an unpurified water-wet pulp obtained by interacting aniline with disodium 4,4'-bis(4,6-dichloro-s-triazin-2-ylamino)-2,2'-stilbenedisulfonate and containing one molecular equivalent excess of aniline for each molecular equivalent of product) was heated for four hours at 155° C with stirring in a stainless steel autoclave. The resulting product, consisting of white rod-shaped crystals, was isolated by filtration and was washed with 500 ml of an aqueous solution containing approximately 0.5 percent sodium chloride.

X-ray diffraction data for the product obtained according to this process corresponded to the data given above for rod form B. Moreover, visual examination, index of refraction values, and X-ray diffraction data showed that the product prepared as described above was from 80 to 100 percent, and probably more than 90 percent in the form of crystalline rod form B.

EXAMPLE 9

A detergent composition containing the crystalline needle form of disodium 4,4'-bis(4-anilino-6-morpholino-s-triazin-2-ylamino)-2,2'-stilbenedisulfonate was prepared as follows. A 100 mg portion of the crystalline needle form was placed in a mortar, 1 ml of 10 percent aqueous sodium chloride solution was added, and the mixture was ground gently for a few seconds to produce a uniform dispersion. There was then added, each in small portions, 20 ml of distilled water and 20 g of a white solid detergent (which consisted of 21.8 percent of a mixture of sodium lauryl sulfate and sodium dodecylbenzenesulfonate, 18.2 percent of sodium sulfate, and 60.0 percent of trisodium phosphate, and which contained no optical bleaching agent) and the resulting mixture was ground until a smooth paste was obtained. This paste was placed in a Petri dish and dried overnight at 80°–90° C. The dry product was ground and passed through 20-mesh and 60-mesh sieves. The solid which passed through the 20-mesh sieve but not through the 60-mesh sieve was retained for testing.

Soap compositions are prepared as above by substituting a soap powder for the detergent employed therein.

The detergent composition described in Example 6 (called herein Sample I) and a detergent composition identical to the one described in Example 6 except that the amorphous form of 4,4'-bis(4-anilino-6-morpholino-s-triazin-2-ylamino)-2,2'-stilbenedisulfonate was used in place of the crystalline needle form (called herein Sample II) were examined under simulated daylight (using a Macbeth lamp combining incandescent, fluorescent, and ultraviolet lights) and evaluated as to color in comparison with the untreated solid white detergent on the basis of the following scale (which is an arbitrary grading and which validly compares the relative color grades of the samples):

| Color Grade | Definition |
|---|---|
| +2 | Strong brightening effect |
| +1 | Good brightening effect |
| 0 | Color of the untreated white solid detergent |
| −1 | Barely descernible discoloration (ordinarily, a yellowing effect) |
| −2 | Objectionable discoloration or a slight tint |
| −3 | Discoloration stronger than a tint |
| −4 | Any discoloration stronger than the Color Grade designated −3 |

The results of this grading of the sample compositions were as follows:

| | |
|---|---|
| Sample I, | Color Grade of +2 |
| Sample II, | Color Grade of −2 |

Further portions of the detergent compositions Samples I and II prepared as above described were used to launder white cotton swatches at a bath temperature of 49° C for twenty minutes. After completion of the application of the respective test samples to the cotton swatches, each swatch of treated cloth was compared visually and with a Lumetron colorimeter. The results thus obtained showed that Samples I and II each produced a satisfactory whitening and brightening effect on the white cotton swatches.

The laundering treatment was repeated with each of Samples I and II in the above-described manner with the modification that sufficient 5 percent aqueous sodium hypochlorite solution was added to produce a concentration of 0.02 percent of sodium hypochlorite in the wash liquid and after two minutes of the wash cycle one-half the hypochlorite was neutralized with an aqueous sodium sulfite solution. After four minutes, the balance of the hypochlorite solution was neutralized with sodium sulfite and the twenty-minute wash cycle was then completed. As compared with the corresponding test swatches obtained above when no hypochlorite was used, the test swatch washed with Sample I in the presence of hypochlorite showed approximately 47 percent less whitening and brightening effect and the test swatches washed with Sample II showed approximately 60 percent less whitening and brightening effect.

When the crystalline needle form and the amorphous form of disodium 4,4'-bis(4-anilino-6-morpholino-s-triazin-2-ylamino)-2,2'-stilbenedisulfonate were each dissolved in water prior to use, so as to destroy their distinguishing characteristics of physical form, the respective resulting solutions gave essentially identical results as whitening and brightening agents in laundering tests in the presence of sodium hypochlorite as well as in the absence of sodium hypochlorite.

Preparations of disodium 4,4'-bis(4-anilino-6-morpholino-s-triazin-2-ylamino)-2,2'-stilbenedisulfonate wherein the percentage of crystalline needle form was gradually increased gave progressively better test results until the optimum results obtained with the substantially pure crystalline needle form were attained. Thus, for instance, the Color Grade values for white detergent compositions having incorporated therein by the procedure described above 0.5 percent of disodium 4,4'-bis(4-anilino-6-morpholino-s-triazin-2-ylamino)-2,2'-stilbenedisulfonate having the indicated percentages of crystalline needle form and amorphous form were as follows:

| Composition of Test Sample | | |
|---|---|---|
| Crystalline Needles (Percent) | Amorphous (Percent) | Color Grade |
| 100 | — | +2 |
| 90 | 10 | +1.8 |
| 80 | 20 | +1.7 |
| 70 | 30 | +1.3 |
| — | 100 | −2 |

In addition to visual grading, these samples were measured on a Hunter color and color difference meter, Hunterlab Model D25, Hunter Laboratories. As can be seen, to enjoy in practical degree the advantageous properties of the new crystalline needle form, the percentage of the crystalline needle form in the disodium 4,4'-bis(4-anilino-6-morpholino-s-triazin-2-ylamino)-2,2'-stilbenedisulfonate should be at least about 80 percent, and is preferably 95–100 percent.

EXAMPLE 10

A detergent composition containing the novel crystalline needle form of disodium 4,4'-bis(4,6-dianilino-s-triazin-2-ylamino)-2,2'-stilbenedisulfonate described in Example 7 was prepared as follows:

An accurately weighed sample of 62 mg. of the novel crystalline needle form of the compound was placed in a mixing tube along with one ml of 0.1N aqueous sodium hydroxide solution. The mixture was triturated for 30 seconds with a motor-driven pestle. Twenty grams of the solid white detergent (which consisted of 21.8 percent of a mixture of sodium lauryl sulfate and sodium dodecylbenzenesulfonate, 18.2 percent of sodium sulfate, and 60.0 percent of trisodium phosphate, and which contained no optical bleach) and 20 ml of water were then added and the mixture was triturated again until a smooth paste was obtained. The mixture was then placed in a Petri dish and dried overnight at 90°–100° C. The cake was broken up with a spatula, and the chunks were forced through a 20-mesh sieve. The screened material was collected on a 60-mesh sieve and shaken to remove the fines. The brightener-detergent composition retained on the 60-mesh screen was used for testing.

In the foregoing manner three detergent compositions were prepared containing, respectively, the crystalline rod form of disodium 4,4'-bis(4,6-dianilino-s-triazin-2-ylamino)-2,2'-stilbenedisulfonate (Sample III), the crystalline plate form of the compound (Sample IV), and the amorphous form of the compound (Sample V).

The detergent composition Samples III, IV and V were examined under simulated daylight (using a Macbeth lamp combining incandescent, fluorescent, and ultraviolet lights) and evaluated as to color in comparison with the untreated solid white detergent on the basis of the scale described in Example 9. The results of this grading of the sample compositions were as follows:

| Sample III, | Color Grade of +1 |
| Sample IV, | Color Grade of −2 |
| Sample V, | Color Grade of −3 |

When the above tests were repeated using various grades of commercially available disodium 4,4'-bis(4,6-dianilino-s-triazin-2-ylamino)-2,2'-stilbenedisulfonate in the amorphous and crystalline plate forms, the Color Grade values obtained were consistently −2 and −3. On the other hand, when tested in the same manner, various batches of the novel crystalline rod forms herein described consistently gave values of at least 0; usually there was obtained a value of +1, and occasionally +2.

Further portions of the detergent compositions Samples III, IV and V prepared as above described were used to launder white cotton swatches in a stainless steel cylindrical specimen container in a Launder-O-Meter (a standard laboratory washing machine of the American Association of Textile Chemists and Colorists described in the Technical Manual and Year Book of the Association, Howes Publishing Co., Inc., New York, N.Y., Volume XXVIII, 1952, pages 82–83) at a bath temperature of 40° C for twenty minutes. After completion of the application of the respective test samples to the cotton swatches, each swatch of treated cloth was compared visually. The results thus obtained showed that Samples III, IV and V each produced a satisfactory whitening and brightening effect on the white cotton swatches.

The laundering treatment was repeated with each of Samples III, IV and V in the above-described manner with the modification that sufficient 5 percent sodium hypochlorite solution was added to produce a concentration of 0.01 percent of sodium hypochlorite in the wash liquid and after 2 minutes of the wash cycle the hypochlorite was neutralized with an aqueous sodium hydrosulfite solution, and the 20-minute wash cycle was then completed. As compared with the corresponding test swatches obtained above when no hypochlorite was used, the test swatch washed with Sample III in the presence of hypochlorite showed approximately 5 to 10 percent less whitening and brightening effect and the test swatches washed with Samples IV and V respectively showed in each instance approximately 75–80 percent less whitening and brightening effect.

When the crystalline rod, crystalline plate, and amorphous forms of disodium 4,4'-bis(4,6-dianilino-s-triazin-2-ylamino)-2,2'-stilbenedisulfonate were each dissolved in water prior to use, so as to destroy their distinguishing characteristics of physical form, the respective resulting solutions gave essentially identical results as whitening and brightening agents in laundering tests in the presence of sodium hypochlorite as well as in the absence of sodium hypochlorite.

Preparations of mixtures of the amorphous form and the rod forms of disodium 4,4'-bis(4,6-dianilino-s-triazin-2-ylamino)-2,2'-stilbenedisulfonate wherein the percentage of crystalline rod form was gradually increased gave progressively better test results until the optimum results obtained with the substantially pure crystalline rod form were attained. Thus, for instance, the Color Grade values for white detergent compositions having incorporated therein by the procedure described above 0.3 percent of disodium 4,4'-bis(4,6-dianilino-s-triazin-2-ylamino)-2,2'-stilbenedisulfonate having the indicated percentages of crystalline rod form and amorphous form were as follows:

| Composition of Test Sample | | |
| --- | --- | --- |
| Crystalline Rods (Percent) | Amorphous (Percent) | Color Grade |
| 100 | — | +1 |
| 90 | 10 | 0 |
| 80 | 20 | −1 |
| 70 | 30 | −2 |
| — | 100 | −3 |

As can be seen, to enjoy in practical degree the advantageous properties of the new crystalline rod forms, the percentage of the crystalline rod forms in the disodium 4,4-bis(4,6-dianilino-s-triazin-2-ylamino)-2,2'-stilbenedisulfonate should be at least about 80 percent, and is preferably 90–100 percent.

The fact that the above-noted beneficial effects of crystalline rod formation of disodium 4,4'-bis(4,6-dianilino-s-triazin-2ylamino)-2,2'-stilbenedisulfonate are not ascribable to mere purification of the amorphous product was demonstrated by the following procedures: 200 parts of disodium 4,4'-bis(4,6-dianilino-s-triazin-2-ylamino)-2,2'-stilbenedisulfonate in the form of crystalline rod form B were refluxed in 800 parts of 60 percent aqueous acetone, containing sufficient sodium hydroxide to give a basic reaction to phenolphthalein, until the product was completely dissolved. Hydrochloric acid was then added until the pH of the mixture was 7.0, and the solvent was removed by distillation until the pot temperature was 73° C. At this point the pH of the mixture was 6.3. The precipitated product was removed by filtration and washed with 2 percent sodium chloride solution. The filter cake was reslurried in 2000 parts of 2 percent chloride solution at room temperature and filtered and washed as before. The dried product was yellow and amorphous, as determined by visual examination under a microscope.

Eleven and one-tenth parts of the above yellow amorphous form of disodium 4,4-bis(4,6-dianilino-s-triazin-2-ylamino)-2,2'-stilbenedisulfonate was suspended in 150 parts of water containing sufficient sodium hydroxide to bring the pH of the mixture to 11.0. The mixture was heated to 98°–99° C and aniline was added in small portions until the mixture contained a total of five parts of aniline. After approximately one hour, the suspension returned to a white color. The small crystals which had formed were found to have the crystalline structure of rod form A.

Another portion of 22.3 parts of the yellow amorphous form of disodium 4,4'-bis(4,6-dianilino-s-triazin-2-ylamino)-2,2-stilbenedisulfonate described above was slurried in 220 parts of water containing sodium hydroxide slightly greater than pH 11. Three and one-tenth parts of aniline, 2 parts of sodium chloride and 1 part of 20 percent aqueous nonylphenylpolyethylene glycol ether surface active agent were then added. The mixture was washed into an autoclave with 133 parts of water and heated at 150° C for 2 hours. An additional 1.5 parts of aniline were added, and the autoclaving was continued at 150° C for one hour. The white crystalline product which had formed was filtered and washed with 400 ml of 1 percent sodium chloride solution. When dried, the product was found to have the crystalline structure of rod form B.

Thus, rod form B was converted to the undesirable amorphous form, and the amorphous form reconverted both to rod form A and rod form B. In the amorphous form, prepared by simple precipitation of a solution of dissolved rod form B crystals, the characteristic undesirable properties (i.e., poor Color Grade and bleach resistance) had returned, thus demonstrating that those properties were not ascribable to impurities. Accordingly, regardless of the manner in which the novel rod forms A and B are formed, the same results are obtained.

We claim:

1. A detergent composition consisting essentially of a detergent and an effective brightening amount of the compound disodium 4,4'-bis(4,6-dianilino-s-triazin-2-ylamino)-2,2'-stilbenedisulfonate in the form of birefringent crystalline rods in which the lowest index of refraction has a value between 1.53 and 1.54 and is parallel to the long axis, said rods being characterized by the following X-ray diffraction data:

| INTERPLANAR SPACINGS, A |
| --- |
| 6.23 |
| 5.90 |
| 5.70 |
| 5.59 |
| 5.51 |
| 5.34 |
| 4.90 |
| 4.85 |
| 4.60 |
| 3.98 |
| 3.82 |
| 3.64 |
| 3.44 |
| 3.28 |
| 3.22 |

2. A detergent composition consisting essentially of a detergent and an effective brightening amount of a new article of manufacture which is the compound disodium 4,4'-bis(4,6-dianilino-s-triazin-2-ylamino)-2,2'-stilbenedisulfonate wherein approximately 80 to 100 percent of said compound is in the form of birefringent crystalline rods in which the lowest index of refraction has a value between 1.53 and 1.54 and is parallel to the long axis, said rods being characterized by the following X-ray diffraction data:

| INTERPLANAR SPACINGS, A |
| --- |
| 6.23 |
| 5.90 |
| 5.70 |
| 5.59 |
| 5.51 |
| 5.34 |
| 4.90 |
| 4.85 |
| 4.60 |
| 3.98 |
| 3.82 |
| 3.64 |
| 3.44 |
| 3.28 |
| 3.22 |

3. A detergent composition consisting essentially of a detergent and an effective brightening amount of a novel crystalline rod form of a bis-triazinylaminostilbene of the formula

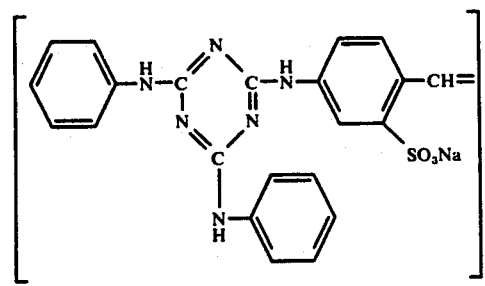

which is prepared by subjecting the amorphous or ordinary crystalline forms thereof to a temperature of at least 155° C in aqueous aniline medium at superatmospheric pressure in an autoclave for several hours to convert it to the novel crystalline form.

* * * * *